United States Patent [19]

Milford et al.

[11] Patent Number: 4,517,289

[45] Date of Patent: May 14, 1985

[54] MONOCLONAL ANTIBODIES FOR HUMAN TISSUE CROSS-MATCHING

[75] Inventors: Edgar L. Milford, Dover; Charles B. Carpenter, Weston; Jean M. Paradysz, Brighton, all of Mass.

[73] Assignee: Brigham and Women's Hospital, Boston, Mass.

[21] Appl. No.: 409,183

[22] Filed: Aug. 18, 1982
(Under 37 CFR 1.47)

[51] Int. Cl.$^3$ .................... G01N 33/54; C12N 5/00; C12N 15/00; C12R 1/91; A61K 39/395
[52] U.S. Cl. ........................ 435/7; 435/240; 435/810; 435/172.2; 435/948; 260/112 B; 260/112 R; 436/548; 436/821; 935/96; 935/103; 935/110
[58] Field of Search ............ 435/7, 172, 948, 240, 435/172.2; 436/548, 821; 260/112 R, 112 B

[56] References Cited

U.S. PATENT DOCUMENTS 4,314,026  2/1982  Descamps-Latscha ............... 435/7
4,350,683  9/1982  Galfrè et al. .......................... 435/7

OTHER PUBLICATIONS

McKearn et al., *Monoclonal Antibodies*, Plenum Publishing Co., N.Y. (1981), 219-234.
Howard et al., Immunol., 41:131-141, (1980).
Parham et al., Nature, 276:397-398, (1978).
Parham et al., J. Immunol., 123,(1):342-349, (1979).
Haynes et al., PNAS, USA, 76(11):5829-5833, (1979).
Eisen, *Immunology*, Harper & Row, Hagerstown, Md., 618, (1974).
Smilek et al., *Journal of Experimental Medicine*, 151, May 1980, pp. 1139-1150, "Monoclonal Rat Anti-Major Histocompatibility Complex Antibodies Display Specificity for Rat, Mouse, and Human Target Cells".
*Nature*, 266, Apr. 1977, pp. 550-552, Galfre et al., "Antibodies to Major Histocompatibility Antigens".

*Primary Examiner*—Esther M. Kepplinger
*Attorney, Agent, or Firm*—Oblon, Fisher, Spivak, McClelland & Maier

[57] ABSTRACT

Immortal, antibody-producing, hybridomally-produced clones which produce antibodies that react specifically with human HLA antigens and which are produced from rat lymphocyte cells sensitized against cells from a rat strain having different histocompatibility antigens are disclosed along with methods of producing the clones and antibodies and methods of using the antibodies in tissue crossing tests.

12 Claims, No Drawings

MONOCLONAL ANTIBODIES FOR HUMAN TISSUE CROSS-MATCHING

BACKGROUND OF THE INVENTION

1. Field of the Invention

The present invention relates to hybridoma cell lines and to monoclonal antibodies produced thereby that are specific for antigens coded by the HLA gene complex and therefore are useful in the typing of human tissue that is to be used in organ transplants.

2. Description of the Prior Art

Transplantation of human organs, particularly the kidney, has become a relatively common procedure. Ideally, the donor organ is obtained from an identical twin since the antigens of the donor and recipient in such a case are identical and no histoincompatibility exists. Therefore, no immune response to the graft occurs in such a transfer, known as an isograft. However, most transplants are between two less closely related individuals of the same species and histocompatibility differences in such an allograft may be stong or weak, depending on the individuals. The fate of transplanted tissues and organs depends on a number of factors, but the recipient's immune response to graft antigens is the central event. Definition of antigenic systems which serve as strong barriers to transplantation has therefore become a major investigational interest, having both practical application in clinical transplantation and theoretical value in understanding the natural role of the histocompatibility antigens in immunobiology.

A single chromosomal gene complex codes for the major histocompatibility antigens in each vertebrate species investigated so far. In humans the histocompatibility antigens are produced by the HLA gene complex. This complex occupies a portion of the short arm of the human C6 chromosome and consists of several series of paired alleles which are inherited from generation to generation in a dominant fashion, segregating randomly from other important antigens such as the ABH red blood cell type groups.

Antigens of the HLA system are divided into two classes. Each class I antigen consists of an 11,500-dalton $\beta_2$-microglobulin sub-unit and a 44,000-dalton heavy chain which carries the antigenic specificity. Three gene loci (A, B and C) are recognized for the class I antigens. There are over 60 clearly defined A and B specificities while 8 C locus specificities are known. Evidence that this gene complex plays the major role in the transplantation response comes from the fact that haplotype-matched sibling donor-recipient combinations show excellent results in kidney transplantation, in the vicinity of 85% to 90% long term survival.

A non-serologically defined antigen, responsible for the mixed lymphocyte response, is caused by a distinct locus called D. Although D-locus antigens are not as yet clearly identifiable by serotyping techniques, serologically defined specificities closely related to the D-locus have been defined. These have the special property of not being expressed on platelets or unstimulated T lymphocytes. These specificities are termed class II, having two glycoprotein chains of 29,000 ($\beta$) and 34,000 ($\alpha$) daltons and lacking $\beta_2$ globulin. These antigens are also termed HLA-DR (D-related) and are important in tissue typing.

Tissue typing is currently being carried out using sera obtained from multiparous women. A major problem exists because of the unreliability of this source. Only a limited amount of antibody is available from any one woman. Accordingly, it is necessary to continually replace standard antibodies with new antibodies which must be standardized and checked against the previously existing ones. Furthermore, because of the heterogeneous nature of antibodies obtained in this fashion, cross-reactivity is a major problem. Accordingly, there have been many attempts to produce antibodies more suitable for crossmatching by immunological techniques. Several such attempts involve xenoimmune (cross-species) sera to detect allospecificity in the antigen-donor species. Examples include rabbit anti-human antibodies by Einstein et al, Transplantation 12:299 (1971) and Ferrone, Tissue Antigens 12:153 (1978) and monkey anti-human antibodies by Sanderson et al, Transplant. Proc. 2:163 (1974). The most specific anti-HLA serum appears to be a rabbit anti-A9 serum prepared by immunization with A9 antigen purified from human serum or urine (see Ferrone et al, Tissue Antigens 5:41 (1975)). However, A9 is actually a common determinate of A23 and A24, and thus possibly the allele-specific major epitope is not the only target with which this antibody reacts.

The advent of hydridomal techniques has brought about the possibility of producing homogeneous populations of highly specific antibodies gainst a variety of antigens. Koprowski et al, U.S. Pat. No. 4,172,124, describes antibodies produced by somatic cell hybrids between myeloma cells and spleen or lymph cells that are specific for malignant tumors. Koprowski et al, U.S. Pat. No. 4,196,265, describes continuous cell lines of genetically-stable fused-cell hybrids capable of producing large amounts of IgG antibodies against specific viruses, such as influenza virus, rabies, mumps, SV40 and the like. Zurawski et al, Federation Proceedings 39: 4922 (1980), discloses hybridomas producing monoclonal IgG antibodies against tetanus toxin. Monoclonal antibodies have also been described against human tumor cells, Yeh et al, Proc. Nat. Acad. Sci. 76: 2927 (1979); human T lymphocyte subsets, Reinberz et al, Proc. Nat. Acad. Sci. 76: 4062 (1979) and malaria parasites, Nussenzweig et al, Science 207: 71 (1980).

The prior art most closely related to this application appears to be McKearn et al, "Rat-Mouse Hybridomas and Their Application to Studies of the Major Histocompatibility Complex," in *Monoclonal Antibodies*, Kennett et al, eds. Plenum Publishing Co., N.Y. (1981), which discloses the use of rat-mouse hybridomas and their application to studies of the histocompatibility complex in various species. Several rat-mouse hybridomas producing rat anti-rat antibodies were reactive with determinants on cells from other species, such as humans. Four of nine hybridoma antibodies were reactive with periphrial blood lymphocytes from randomly chosen humans in a complement-mediated cytotoxicity assay. However, a later study by the same investigators indicated that these antibo dies were not useful in identifying private determinants of the HLA locus since no correlation between specific HLA antigens and the hybridomally produced antibodies occurred.

Accordingly, there still exists a need for monoclonal antibodies suitable for tissue matching.

SUMMARY OF THE INVENTION

Accordingly, it is an object of this invention to provide a hybridoma cell line and an antibody produced thereby useful for the tissue typing of human tissues.

It is a further object of this invention to provide a method of producing such antibodies in an efficient manner.

These and other objects of the invention as will hereinafter become more readily apparent have been accomplished by providing an immortal, antibody-producing, hybridomally-produced clone and an antibody produced thereby, wherein said antibody is an immunoglobulin specific for an antigenic determinant encoded by an HLA gene complex in humans and said clone is produced by an immortal cell line fused with a lymphocyte obtained from a first rat immunized against cells obtained from a second rat having a different histocompatibility antigen.

DESCRIPTION OF THE PREFERRED EMBODIMENTS

Cell lines prepared by the procedures described herein are exemplified by cultures now on deposit with the American Type Culture Collection, 12301 Parklawn Dr., Rockville, Md. 20852, U.S.A. These cultures were deposited on Aug. 10, 1982, and are identified by ATCC #HB8156 and ATCC #HB8157.

Although it was known prior to the present invention that monoclonal antibodies can be produced against various antigens, it was not known whether monoclonal antibodies produced from cells of one rat immunized against cells from a second rat having different rat histocompatibility antigens would be specific for private determinants of a human HLA gene locus. Previous investigators from other laboratories had found that monoclonal antibodies produced in this fashion were not suitable.

The present inventors worked under the hypothesis that the difficulty in finding polymorphic anti-histocompatibility antigen reagents by direct sensitization of mice (or rats) with human lymphoid cells is a consequence of the large number of species-specific determinants which are discrepant in man and murines. The inventors further hypothesized that there might be conservation from rat to man of the polymorphic-specific determinants (alloantigens) which are perceived as foreign between individual of the same species. Hence, a rat antibody against an alloantigenically different rat might recognize antigens which are present on some, but not all, humans.

The investigators sought to confirm conservation of private histocompatibility antigens by testing Wistar Furth rat anti-Lewis rat monoclonal antibodies against an extended panel of human cells. These reference cells had been pre-typed with standard NIH tissue-typing trays to determine their HLA-A, B and C and DR antigens, the so-called class I and class II antigens, respectively. The tissue and strain distribution of several subclones indicated that these antibodies detected polymorphic class I antigens on the Lewis rat. This fact, combined with the fact that the isotype of both antibodies was IgM and hence more likely to be cytotoxic, led the investigators to use these monoclonals in a human screening test.

The invention is practiced by producing a hybrid cell line from an immortal cell line and an antibody producing rat lymphocyte that has been stimulated to form antibodies against cells from a second rat strain which has one or more different histocompatibility antigens. Since primary antigenic differences between strains of rats are caused by differences in the histocompatibility complexes, most of the antibodies produced will be reactive with rat histocompatibility antigens. This step eliminates problems caused by the xenoantigenic reactivity that occurs when human cells are used to induce antibody formation in a different species. Since the inventors have demonstrated by the work disclosed herein that there is conservation between rat and human histocompatibility antigens, this method of producing monoclonal antibodies is more efficient than previously known methods for producing antibodies against the HLA complex of humans.

Many different techniques of hybridoma formation and monoclonal antibody production are known and may be applied in carrying out the objects of the invention. In general, the process comprises sensitizing an animal with an antigen to induce an immune response, obtaining immune cells from the animal, and fusing the immune cells with a malignant cell line using one of a variety of fusing agents. Resulting hybrids are then grown in a medium which precludes the expansion of the original malignant cell line. After an initial period during which non-hybrid cells die, growing hybrids may be observed microscopically. Each of these colonies is assayed for the immune function sought. Colonies which demonstrate antibody secretion against one or more HLA determinant are cloned. These clones are then grown in large quantity, for example by stepwise transfer to larger wells, flasks, and bottles. Each of these steps is discussed in somewhat greater detail in the following paragraphs. However, it will be recognized by a practitioner in the area of hybridoma technology that many modifications and additions may be made to the techniques included in this discussion, which is intended to be exemplary and not limiting, while remaining within the scope of the present invention.

The first step of raising monoclonal hybrids is generally immunization of an animal. Because fusion occurs preferentially with proliferating cells, it is preferred to schedule immunization to obtain as many immunoblasts as possible, with harvesting occurring about 3–4 days after the last inoculation being most preferred. In the present application suitable antigens for use in immunization are present on the cell surface of rat lymphoid cells. Accordingly, lymphoid cells are obtained from a rat which differs from the responder rat in its histocompability antigens. It is preferred to use rat strains which differ only in their histocompatibility antigens and are otherwise isoimmunogenic. The major histocompatibility complex antigens of many rat strains are known and if not known can be determined by known techniques, such as those described later in this application.

The immunization schedule may entail two or more injections, at intervals of up to a few weeks, with the last injection being three to four days before the fusion. Adjuvants, such as water-in-oil emulsions (Freund's adjuvant), may be included if desired and are preferred for the initial injection. It is also possible to employ immune cells which have been sensitized naturally or to carry out in vitro sensitization of either B or T lymphocytes.

The cell line chosen for hybridization should be capable of rapid growth, be deficient in its metabolism for a component of the growth medium, and have potential for good fusion frequency. The species from which the immortalizing line is derived should be closely related to the species from which the antibody-producing cell is obtained. Intraspecies fusions, particularly between like strains, work better than interspecies fusions. However, rat immortal cell lines have not been as well developed as mouse cell lines and rat-mouse hybrids have proven suitable for the purposes of this invention.

Readily available cell lines, many of which are mutants selected for their inability to secrete immunoglobulin, include the following:

1. P3-NS1-1-Ag4-1, or NS1, a variant of the $P_3$ ($MOPC_{21}$) mouse myeloma line.
2. $MPC_{11}$-X45-6TG, or X45, a Balb/c mouse plasmacytoma.
3. P3-X63-Ag8, or X63, the mouse myeloma cell line originally used by Kohler and Milstein. Recent mutants have been developed (e.g. X63-Ag8.653) which no longer secrete immunoglobulins.
4. sp2/0-Ag14, another BALB/c mouse myeloma line.
5. GD-36-A.Ag1 lymphoblastoid cell line obtained by injection of SV40 virus into Syrian hamsters.
6. Subclone Y3 - Ag 1.2.3., or Y3, from the rat myeloma mutant 210.RCY3.Ag1.

With the growth of hybridoma technology, new immortal cell lines suitable for hybrid formation are continually being developed. Such cell lines are also suitable for carrying out the hybridization processes described in connection with the present invention.

Once immune cells are obtained and a suitable immortal cell line chosen, the cells are fused to form the hybrid cell line. Various techniques are available for inducing fusion and include virus-induced fusion and polyethyleneglycol-induced fusion. Inactivated Sendai virus is preferred for virus-induced fusion. Other viruses can induce fusion of somatic cells if the two parental cells are both susceptible to the virus. Among suitable viruses are HVJ and Epstein-Barr virus.

Polyethyleneglycol (PEG) can also be used as a fusing agent. PEG itself is toxic for cells at high concentrations and various concentrations should be tested for effects on viability before attempting fusion. PEG having average molecular weights varying from 1000 to 6000 may be used with an average molecular weight of about 1500 being preferred. PEG should be diluted to 30–50% with saline or serum-free medium. Since PEG is toxic for the cells, the time exposure to PEG should be limited. Exposure to PEG for 1–10 minutes, preferably 3–7 minutes, is best for many cell lines.

Other conditions that should be controlled for increased fusion efficiency are temperature and cell ratios. Extremes of temperature should be avoided during fusion. Fusion at 4°–10° C. is preferred with fusion at about 4° C. being most preferred. Preincubation of each component of the fusion system at about 4° prior to fusion is preferred. The ratio between spleen cells and malignant cells should be optimized to avoid self-fusion among spleen cells. Myeloma/spleen-cell ratios ranging from 2:1 to 1:20 are suitable, with 1:1 to 1:10 being preferred and about 1:4 being most preferred.

The mixture of cells obtained after fusion contains hybrids, fused and unfused parental spleen cells, and malignant cells. Spleen cells cannot maintain growth in routine culture medium and will eventually die out. Malignant cells would keep on dividing and soon overgrow the hybrids unless a selective medium is used that will allow only the growth of hybrids. The malignant cell lines must therefore be selected so that they are unable to grow on the chosen culture medium. For example, several available cell lines are hypoxanthine guanine phosphoribosyl transferase (HGPRT) deficient and will not grow in aminopterine-containing medium because of their inability to synthesize purines from thymidine and hypoxanthine. Some HGPRT+ revertants may occur among the malignant cells and these should be periodically purged with 8-azaguanine (8-AZA). The selection medium used to allow only growth of hybrids is composed of hypoxanthine, $1\times10^{-4}$M; aminopterine, $4\times10^{-7}$M; and thymidine, $1.6\times10^{-5}$M (HAT medium). Other culture media and deficient cell lines may also be used in the practice of the invention.

The fusion mixture can be grown in HAT medium immediately after fusion or at a later time. The feeding schedules for the fused cells may vary, but obligatory feeding of HAT medium (or another deficient medium) once or at intervals, for example on days 1, 6, and 11, is required, followed by growth in either regular culture medium or a medium containing hypoxathine and thymidine. A single feeding of HAT medium is preferred.

Standard tissue culture medium may be used to support the growth of hybrids. Good results may be obtained with Iscove's medium, Dulbecco's modified Eagle's medium (DMEM), or HY medium: DMEM enriched with 4.5 g glucose/liter, 10% NCTC 109, 20% serum, and 0.15% glutamine. HT medium (HAT medium without aminopterine) is preferred.

Serum used in media should be tested for its ability to support the growth of the malignant cell line prior to use. Hybrids may grow in, for example, horse or calf serum, but fetal bovine serum has no immunoglobulin, an important consideration that makes screening for antibody-producing cells much easier, and is therefore preferred. Hybrids may also be grown in serum-free media supplemented with 10–20% of a serum albumin, e.g., bovine serum albumin, and trace elements.

Feeder cells may be used in the initial stages of cell growth to enhance the survivability of the isolated cells. Irradiated thymocytes, spleen cells, myeloma cell lines, and mouse peritoneal macrophages may be used for feeder layers. Preferred feeder cells for use with rat-mouse hybrids are irradiated thymocytes from the rat fusion (responder) stain.

Rapid identification of antibody-producing hybrids is important in order to avoid expenditure of time and resources on cultivation of extraneous cells. Early detection of hybridoma antibodies specific for cell surface antigens may be performed using standard immunological assays, for example, the eosin dye exclusion microcytotoxicity assay. This test is described in greater detail later in this application. Briefly, antiserum and mineral oil are placed into each of the test wells of a test tray. Normal human serum is placed in control wells. Target cells are placed into each cell, the trays are incubated, and complement is added to each well. After additional incubation, the wells are treated with eosin dye and formaldehyde fixative. Cytotoxicity is then determined microscopically. This assay technique is not a part of the present invention and other assay techniques which reveal specificity of the antibody for antigens encoded by private determinants of human cells may be substituted for this technique if desired.

It is preferred that cells selected for cloning produce an antibody that is specific for a single HLA antigen although less selective antibody may also be useful for identifying groups of antigens. A "specific antibody" is one that reacts positively (as measured by any test capable of distinguishing positive and negative antibody interactions, such as the eosin dye test descsribed above) with a particular antigen or group of antigens at specified antibody and antigen concentrations while it reacts negatively with other antigens under the same conditions.

Hybrids obtained by fusion are often initially heterogeneous colonies. In order to obtain a homogeneous (monoclonal) cell line these colonies must be cloned. By this is meant the process of achieving growth of a cell line from a single parental cell. Cloning of hybrids is preferably performed as soon as a confluent monolayer occurs in the sample well. Later cloning of hybrids usually results in colonies which are slow growers and low yielders of antibody.

Cloning can be performed by the limiting dilution method in fluid phase or by directly selecting single cells growing in semi-solid agarose. For limiting dilutions, cell suspensions are diluted serially to yield samples which have a statistical probability of having only one cell per well. The agarose technique begins with seeding of cells in a semi-solid upper layer of agarose over a lower layer containing feeder cells. The colonies from the upper layer are picked up and transferred to individual wells. Feeder cells, such as irradiated peripheral lymphocytes, can be used to improve the cloning efficiency.

Antibody secreting hybrids grown in tissue culture flasks generally yield a supernatant with an antibody concentration in the range of 50–200 $\mu$g/ml. It is generally not desirable to use the ascites method to increase antibody concentration.

Antibodies may be purified by any of the standard techniques of protein separation such as differential precipitation using, for example, ammonium sulfate; electrophoresis; chromatographic separation based on molecular size, such as Sephadex chromatography; or various techniques based on binding properties of or to the antibodies, such as affinity chromatography. Complete purification is not required since only the desired immunoglobulin is present and other components do not generally interfere with its immunological action.

A particularly preferred sequence for the production of monoclonal antibodies is described in the following paragraphs. Wistar-Furth (WF) rats are immunized by an initial intravenous injection of about 10 million lymphoid cells obtained from Lewis (LEW) rats followed by an intervenous injection of the same material approximately 1 month later. Cells are taken from the spleens of the primed and boosted rats three or four days after the second injection in order to obtain dividing B cells for fusion. Other rat strains may be substituted for either or both of the strains mentioned here in order to produce antibodies of different specificities.

A preferred myeloma cell line for fusion is P3-NSI/-AG 4-1 (NS1), which is an azaguanine resistant, non-secretor myeloma line previously described by Kohler and Milstein, Eur. J. Immunol. 6:511 (1976). When fused it produces $\kappa$ chains. Fifty percent polyethylene glycol (PEG-1500) is preferred as a fusion promotor. Spleen cells are fused with the NS1 cell line at 4° C. at a ratio of 4 spleen cells to 1 NS1 cell. The NSI/spleen-cell mixture is washed in serum-free RPMI 1640 medium, spun at 1500 rpm for 10 minutes, and the supernatant decanted. Between 2 and 5 ml of a sterile solution of 50% polyethylene glycol (PEG-1500) which has been pre-screened for fusion efficiency is added to the pellet, the pellet is loosely resuspended by vibrating the bottom of the tube, and the cells are immediately pelleted at 4° C. for 8 minutes at 400$\times$g. The fused cells are cleaned by decanting the polyethylene glycol and washing them three times in serum-free medium prior to resuspending at 5–10 million per ml in HT medium. Cells which have been fused are plated onto a flat-bottomed microtiter plate at 50,000 cells/ml in a volume of 0.1 ml HT medium. The cells are allowed to grow for 24 hours in a moisturized 5% $CO_2$ atmosphere at 37° C. The cells are then grown in selective HAT medium until macroscopic clones appear in the wells. This is accomplished by feeding the wells with 2 drops of HT medium supplemented with 4% aminopterin (HAT). Wells are observed daily for evidence of clone growth and acidification of the medium, and the HAT medium replaced as necessary. When clones become confluent over the surface of the flat bottoms, the supernatent is removed and screened for specific antibody activity. Positive wells are preserved by transfer of the cellular contents to multiple flat-bottom microtiter plate wells.

Positive wells are sub-cloned in soft agar over a feeder layer of irradiated thymocytes from the responder rat strain using the limiting dilution technique. A semi-solid agarose supplemented with 50% NS1 cell supernatent and 20% fetal calf serum is used. Optimal cloning density is about 2–5 thousand cells per Linbro plate well. The cells are suspended in the agarose cloning solution at 45° C. and immediately distributed onto Linbro plates at 2 ml per plate. After culture for 1 to 2 weeks at 37° C., an average of 1 to 2 macroscopic clones per wells appears. These macroscopic clones are taken from the wells with a sterile pasteur pipette and expanded in HT medium prior to retesting the supernatant for persistant antibody activity.

The hybridomally-produced anti-HLA antibodies of the present invention can be used in any of the array of available assays used in tissue typing. The present invention is not limited to any of these techniques in particular as they are not considered to be part of the invention. One suitable technique is the standardized eosin dye exclusion microtoxcicity test as described in the AACHT Techniques Manual. In this test one microliter of anti-serum is placed in each well of a 72- or 96-well Terasaki tray after the tray is loaded with 5 microliters of mineral oil per well. Normal human serum is placed in control wells. Target cells obtained from the person whose tissue is being cross-matched are placed into each well at 2,000 per well at a volume of 1 microliter. Lymphocytes, obtained from the peripheral blood system, spleen, or lymph glands, are preferred target cells. The trays are incubated for 1 hour at 22° C., and 5 microliters of rabbit complement is added to each well. The trays are incubated for an additional 2 hours at 22° C. and then flooded with 5 microliters of eosin dye (buffered) and formaldehyde fixative. The trays are covered with a glass slip and sealed with molten paraffin prior to reading in an inverted phase microscope. Cells lysis due to a positive reaction is demonstrated by an incursion of dye into the cell interiors.

The previously described cell typing system can be used to assay any type of cell but is particularly preferred for use with human lymphocytes in the course of tissue typing.

The antibodies of the invention can be prepared in kit form ready for use in an assay procedure. The kit will contain the antibody in any stable form, for example, lypholized, frozen, or in solution, along with any other necessary reagents and accessories, such as tissue antigen standards; reaction vessels, such as plastic tubes or trays; and sample transfering devices, such as pipets. Many such kits are now available for other immunoassays, and the manufacturing of such kits is now standard practice.

Having now generally described this invention, the same will be better understood by reference to certain specific examples which are included herein for purposes of illustration only and are not intended to be limiting of the invention or any embodiment thereof, unless specified.

EXAMPLES

Example 1: Preparation of Monoclonal Antibodies
Materials

8-Azaguanine (8-AZA) selective medium for the NS1 myeloma line is made up with 500 ml RPMI medium, 1% gentamicin, 1% 8-AZA (15 micrograms/ml), 10% fetal calf serum (FCS), and 1% glutamine (200 mM solution in 0.85% NaCl solution stock)

Hypoxanthine-thymidine stock (100×) is made up by adding 408 mg hypoxanthine to 100 ml distilled water (adding NaOH until dissolved). Thymidine (114 mg) is dissolved in 100 ml of distilled water. Hypoxanthine and thymidine solutions are combined and made up to 300 ml with distilled water. The pH is adjusted to 10.0 with acetic acid, filtered and aliquoted in 5 ml samples (stored at −70° C.)

Aminopterin stock is made by dissolving 8.8 mg of aminopterin in 500 ml of distilled water. The pH is adjusted to 7.5 to 7.8 with 0.5 N acetic acid, and the preparation filtered, aliquoted in 2 ml and stored at −20° C.

OPI stock solution is made at 100× by mixing oxaloacetic acid (1500 mg), pyruvic acid (500 mg), and bovine insulin (200 U; 74.5 mg), and dissolving by bringing to 1000 ml in distilled water. HCl is added to dissolve the insulin. Two ml aliquots are stored at −20° C.

HT medium is made as follows Dulbeccos minimal essential medium (375 ml), NCTC medium (50 ml), OPI stock (5 ml), L-glutamine (10 ml), HT stock (5 ml), gentamicin (5 ml of 10 mg/ml stock), and fetal calf serum (50 ml). So-called HAT medium consists of HT medium supplemented with 2% aminopterin stock solution.

Immunization Protocol

Wistar-Furth (WF) rats were immunized by an initial intravenous injection of 10 million lymphoid cells from Lewis (LEW) rats followed by an intravenous injection of the same material 30 days afterwards. Cells from the spleens of the primed and boosted rat were taken three days after the second injection for fusion with NS1 myeloma cells as described below.

NS1 Myeloma Cell Line

The NS1 myeloma cell line of Balb/c origin was stored in liquid nitrogen in 20 milion cell aliquots. Cells were thawed at 37° C. and washed twice in plain medium prior to resuspension at 50,000 cells/ml in 8-AZA medium. The cells were allowed to proliferate by incubation at 37° C. in a moisturized 5% $CO_2$ atmosphere in 50 ml plastic culture flasks (Falcon). When the medium became acidic by inspection, the cells were passaged by decanting the old medium and replacing with an equivalent volume of fresh medium.

Fusion Protocol

Wistar-Furth (WF) rats which had been sensitized as described above were sacrificed, exsanguinated, and their spleens removed under sterile conditions. A cell suspension was made in sterile RPMI 1640 medium by cutting the spleen into fine pieces with surgical scissors and expressing it through a 60 guage wire mesh. Erythrocytes were lysed by first pelleting the cells in a 50 ml centrifuge tube, decanting the supernatant and resuspending the cells in 0.083% ammonium chloride solution at 4° C. The cells were incubated for 5 minutes and washed three times in medium with 10% FCS prior to fusion.

Fusion

Balb/c NS1 myeloma cells and WF sensitized spleen cells were both washed in serum free medium and counted. The cell preparations were mixed in a 50 ml centrifuge tube at a ratio of 4 sensitized spleen cells to 1 NS1 cell, spun at 1500 rpm for 10 minutes and the supernatant decanted about 2 to 5 ml of a sterile solution of 50% polyethylene glycol (PEG-1500) which has been pre-screened for fusion efficiency was added to the pellet. The pellet was loosely resuspended by vibrating the bottom of the tube, and the cells immediately pelleted at 4° C. for 8 minuted at 1500 rpm. The fused cells were cleaned by decanting the polyethylene glycol and washing them three times in serum free medium prior to resuspending at 5 to 10 million per ml in HT medium. Cells which had fused were plated onto a flat bottom microtitre plate at 50,000 cells/ml in a volume of 0.1 ml HT medium. The cells were allowed to grow for 24 hours in a moisturized 5% $CO_2$ atmosphere at 37° C. The cells were then grown in selective HAT medium until macroscopic clones apeared in the bottom of the wells. This was accomplished by feeding the wells with two drops of HT medium supplemented with 4% aminopterin stock (HAT). Wells were observed daily for evidence of clone growth and acidification of the medium and the HAT medium replaced as necessary. When clones became confluent over the surface of the flat bottoms, the supernatant was removed and screened for specific antibody activity. Positive wells were preserved by transfer of the cellular contents to multiple flat bottom microtitre plate wells.

Cytopreservation

NS1 myeloma cells and fused hybridoma cells were routinely frozen at varous stages of development as follows. A freezing solution was made composed ot 95% fetal calf serum and 5% dimethylsulfoxide. Up to 20 million cells per ml of freezing solution were suspended and aliquoted in plastic sterile vials and put in a −70° C. freezer for 24 hours followed by storage in liquid nitrogen.

Screening of Clones

The supernatants from primary clones which exhibited exuberant growth were tested in the following ways:

1. Indirect Immunofluorescence—Test cells consisting of nylon wool purified T or B cells were incubated at 4° C. with supernatant for 30 minutes, washed, and counterstained with a fluoresceinated rabbit anti-mouse heavy plus light chain specific immunoglobulin. To avoid cross reaction of the counterstain with immunoglobulin positive B-cells, the cell preparation was preincubated for 30 minutes at 37° C. with a rabbit anti-human immunoglobulin. B-cell surface immunoglobulin was stripped from the cells in this step. Fluorescence positivity was scored by visual inspection under a fluorescence microscope.

2. Eosin Dye Exclusion Microcytotoxicity—Microcytotoxicity was performed using the standard technique for long-incubation crossmatch. Briefly, 1 microliter of antiserum was placed in each well of a 72- or 96-well terasaki tray after the trays were loaded with 5 microliters of mineral oil per well. Normal human serum was placed in control wells. Target cells (human peripheral blood lymphocytes) were put into each well at 2,000 per well in a volume of 1 microliter. The trays were incubated for one hour at 22° C., and 5 microliters of rabbit complement was added to each well. The trays were incubated for an additional 2 hours at 22° C., and then flooded with 5 microliters of eosin dye (buffered) and formaldehyde fixative. The trays were covered with a glass slip and sealed with molten paraffin prior to reading under an inverted phase microscope. Cytotoxicity was scored from 1 to 8 based on percent of cells which faied to exclude the eosin dye ("1" constituting background, and "8" representing 80–100% kill).

Subcloning

To insure that the "clones" were the progeny of one cell, the expanded cell suspensions from hybridoma wells with positive supernatants were subcloned at limiting dilution in semisolid agarose supplemented with 50% NS1 cell supernatant and 20% fetal calf serum. Optimal cloning density was 2–5,000 cells per Linbro plate well. The cells were suspended in the agarose cloning solution (which had been at 45° C.) and immediately distributed into Linbro plates at 2 ml per plate. After culture for 1 to 2 weeks at 37° C., an average of 1 to 2 macroscopic clones per well appeared. These macroscopic clones were taken from the wells with a sterile pasteur pipette and expanded in HT medium prior to re-testing the supernatant for persistent antibody activity.

Example 2: Characterization of Antibody

Once a set of clones whose supernatants have antibody activity against the immunogen was cryopreserved, the antibody activity was characterized to select those with specificity for a determinant peculiar to the cell surface of human subjects. This was done by extensive panel screening against a control panel with known HLA-A, B, C, DR antigens. Both manual analysis of the data and computer-assisted analysis was used to dissect out anti-histocompatibility antigen activity. The subclass of the antibodies recovered was determined by concentrating the supernatant with ammonium sulphate (45%) precipitation, dialysis against normal saline, and ouchterlony gel diffusion precipitation testing with reference·reagents against human immunoglobulin subclasses.

Cell Panel

The Tissue Typing Laboratory (Immunogenetics Section of Brigham and Womens Hospital) has access to a "walking panel" of over 60 normal cell donors of random HLA phenotype. In addition, large numbers of cryopreserved pheripheral blood lymphocytes are available for screening of monoclonal antibodies. Cells of known tissue type from these panels were used to determine antigen specificities.

Analysis of Reaction Patterns

Monoclonal reagents which were positive on immunizing lymphocytes by fluorescence or eosin dye microcytotoxicity were accumulated and multiple "screened trays" established with 1 microliter aliquots of individual supernatants in Terasaki tray wells under 5 microliters of oil. Trays were frozen at −70° C. until use. Each tray was used to establish reaction patterns for the antibody on the test panel cells. Between 30 and 40 individuals were tested to establish the relationship of cytotoxic patterns to HLA. A computer algorithm inspected sera individually for cluster patterns consistent with the known HLA-A, B, C antigens of the cell panel, and provided intermediate matrices useful in manual analysis.

Results

Two monoclonal antibodies, identified by the numbers 3C6 (ATCC #HB8157) and 4F12 (ATCC #HB8156) and produced by the procedure described in Example 1 were specific for private determinants of the HLA antigens. The antibody produced by the cell line 4F12 was specific for the A2 and A11 antigens at high concentrations of antibody while the 3C6 antibody was specific for the A3 antigen. The results of the microcytotoxic panel analysis are shown in Table 1 below.

TABLE 1

MICROCYTOTOXIC PANEL ANALYSIS OF MONOCLONAL RAT ALLOANTIBODIES OF HUMAN T LYMPHOCYTES

| Sample | Antigens | | | | WF Anti-LEW 4F12 | WF Anti-LEW 3C6 |
|---|---|---|---|---|---|---|
| 1 | A11 | A25 | B8 | B18 | + | − |
| 2 | A11 | AX | Bw52 | Bw57 | + | − |
| 3 | A9 | A3 | B7 | BX | − | + |
| 4 | A1 | A3 | B12 | Bw25 | − | + |
| 5 | A25 | A3 | B18 | BX | − | + |
| 6 | A2 | A3 | Bw35 | BX | + | + |
| 7 | A2 | A3 | B12 | B17 | + | + |
| 8 | A2 | Aw19 | B235 | B40 | + | + |
| 9 | A2 | A3 | B7 | BX | + | + |
| 10 | A2 | Aw31 | B13 | B40 | + | − |
| 11 | A2 | Aw31 | B13 | B40 | + | − |
| 12 | A2 | Aw31 | B13 | B40 | + | − |
| 13 | A2 | A29 | Bw35 | B12 | + | − |
| 14 | A2 | Aw24 | Bx | B18 | + | − |
| 15 | A2 | Aw31 | B7 | Bw60 | + | − |
| 16 | A2 | Aw24 | B12 | B18 | + | − |
| 17 | A2 | A1 | B12 | B8 | + | − |
| 18 | A2 | A1 | B7 | Bw16 | + | − |
| 19 | A2 | AX | B7 | B15 | + | − |
| 20 | A2 | A23 | B7 | B8 | + | − |
| 21 | A2 | A10 | B8 | Bw16 | + | − |
| 22 | A2 | A1 | B7 | B12 | − | − |
| 23 | A2 | A1 | B15 | B17 | − | − |
| 24 | A1 | Aw24 | Aw35 | B17 | − | − |
| 25 | Aw24 | Aw30 | B17 | B13 | − | − |
| 26 | A28 | A24 | B18 | Bw35 | − | − |
| 27 | A25 | AX | B18 | Bw35 | − | − |
| 28 | A28 | A24 | B18 | Bw35 | − | − |
| 29 | A1 | Aw24 | Bw35 | B17 | − | − |
| 30 | Aw23 | Aw24 | B14 | Bw35 | − | − |

Statistical analysis using the Chi-square test (shown in Table 2) indicates a high correlation of monoclonal microcytotoxicity with A-locus alloantigens.

TABLE 2

CORRELATION OF MONOCLONAL MICROCYTOTOXICITY WITH A-LOCCUS ALLOANTIGENS

|  | POSITIVE | NEGATIVE |
|---|---|---|
| CROSSMATCH WITH 4F12 | | |
| HLA-A2* OR A11** POSITIVE | 20 (18* + 2**) | 2 |
| HLA-A2 OR A11 NEGATIVE | 0 | 10 |

CHI-SQUARE = 24.2, P < 0.01

| CROSSMATCH WITH 3C6 | | |
|---|---|---|
| HLA-A3 POSITIVE | 5 | 0 |
| HLA-A3 NEGATIVE | 1 | 19 |

CHI-SQUARE = 19.7, P < 0.01

On dilution of the 4F12 antibody, it was discovered that a different specificity occurred at lower concentrations (greater dilutions) of the antibody. At a dilution of 1:64, the antibody reacted strongly with the A29 antigen but not with the A2 or A11 antigens.

TABLE 3

MICROCYTOTOXIC PANEL ANALYSIS OF 4F12 ANTIBODY AT A DILUTION OF 1:64

| Sample | Antigen | | | | Reaction With 1:64 4F12.3 |
|---|---|---|---|---|---|
| 1 | A29 | A10 | B12 | — | + |
| 2 | A29 | A1 | B12 | — | + |
| 3 | A29 | A9 | B12 | B7 | + |
| 4 | A29 | Aw30 | B12 | B13 | + |
| 5 | A29 | A1 | B12 | B7 | + |
| 6 | A29 | Aw24 | B12 | B5 | + |
| 7 | A29 | Aw24 | B12 | B8 | + |
| 8 | A2 | A10 | B12 | — | — |
| 9 | A2 | A3 | B12 | — | — |
| 10 | A11 | A19 | B12 | B5 | — |
| 11 | A2 | A3 | B12 | B7 | — |
| 12 | A2 | — | B12 | B7 | — |
| 13 | A2 | A1 | B12 | — | — |
| 14 | A2 | A1 | B12 | — | — |
| 15 | A9 | A3 | Bw16 | — | — |
| 16 | A1 | — | B8 | — | — |
| 17 | A1 | A2 | B8 | B15 | — |
| 18 | A1 | A2 | B8 | — | — |
| 19 | A1 | A10 | — | — | — |
| 20 | A1 | — | B8 | — | — |
| 21 | A1 | A9 | B8 | — | — |
| 22 | A3 | A28 | B7 | B15 | — |
| 23 | A3 | — | — | B15 | — |
| 24 | A10 | — | B17 | B15 | — |

TABLE 4

CORRELATION OF 1:64 4F12 ANTIBODY WITH A29 ANTIGEN

|  | Positive | Negative |
|---|---|---|
| HLA-A-29 positive | 7 | 0 |
| HLA-A-29 negative | 0 | 17 |

Chi-square = 19.4, P < 0.1

TABLE 5

MICROCYTOTOXICITY OF 4F12 ON CELLS CONTAINING HLA-A2 OR A29 BY TITER*

| Dilution of 4F12 | Cell #54358 (A2, A3, B7, Bw35) | Cell #54384 (A29, A24, B12, B5) |
|---|---|---|
| neat | 8 8 8 8 8 6 | 8 8 8 8 8 8 |
| 1:2 | 6 6 4 4 2 2 | 8 8 8 8 1 1 |
| 1:4 | 6 4 4 2 2 1 | 8 8 8 8 8 8 |
| 1:8 | 2 2 2 2 1 1 | 8 8 8 8 8 8 |
| 1:16 | 1 1 1 1 1 1 | 8 8 8 8 8 8 |
| 1:32 | 1 1 1 1 1 1 | 8 8 8 8 6 6 |
| 1:64 | 1 1 1 1 1 1 | 8 8 8 6 6 6 |
| 1:128 | 1 1 1 1 1 1 | 8 8 8 6 6 6 |
| 1:256 | 1 1 1 1 1 1 | 8 6 6 6 6 4 |
| 1:512 | 1 1 1 1 1 1 | 6 6 6 6 6 4 |
| 1:1024 | 1 1 1 1 1 1 | 8 6 4 4 4 4 |
| 1:2048 | 1 1 1 1 1 1 | 4 4 2 2 2 1 |

*6 replicates per dilution
1 = negative;
2 = 10-19% dead;
4 = 20-39% dead;
6 = 40-79% dead;
8 = 80-100% dead.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A hybridoma cell line selected from a group consisting of ATCC HB8156 and ATCC HB8157.
2. The cell line of claim 1, wherein said cell line is ATCC HB8156.
3. The cell line of claim 1, wherein said cell line is ATCC HB8157.
4. A monoclonal antibody against a human HLA antigen, wherein said antibody is produced by a hybridoma cell line selected from the group consisting of ATCC HB8156 and ATCC HB8157.
5. The antibody of claim 4, wherein said cell line is ATCC HB8156.
6. The antibody of claim 4, wherein said cell line is ATCC HB8157.
7. A method of typing human tissue, comprising the step of:
    contacting an antibody produced by a hybridoma cell line selected from the group consisting of ATCC HB8156 and ATCC HB8157 with cells obtained from a human whose tissue type is being determined.
8. The method of claim 7, wherein said cell line is ATCC HB8156.
9. The method of claim 7, wherein said cell line is ATCC HB8157.
10. A tissue-crossing assay kit, comprising:
    a monoclonal antibody produced by a cell line selected from the group consisting of ATCC HG8156 and ATCC HB8157 and
    a dye.
11. The kit of claim 10, wherein said kit further comprises complement.
12. The kit of claim 10, wherein said kit further comprises a standard human serum reactive with said antibody.

* * * * *